United States Patent
Utterberg

(10) Patent No.: US 6,187,198 B1
(45) Date of Patent: *Feb. 13, 2001

(54) AUTOMATIC PRIMING OF CONNECTED BLOOD SETS

(75) Inventor: David S. Utterberg, Seattle, WA (US)

(73) Assignee: DSU Medical Corporation, Las Vegas, NV (US)

(*) Notice: Under 35 U.S.C. 154(b), the term of this patent shall be extended for 0 days.

This patent is subject to a terminal disclaimer.

(21) Appl. No.: 09/359,366

(22) Filed: Jul. 22, 1999

Related U.S. Application Data

(62) Division of application No. 08/954,804, filed on Oct. 21, 1997, now Pat. No. 5,951,870.

(51) Int. Cl.$^7$ .................................................. B01D 11/02
(52) U.S. Cl. ........................... 210/645; 210/646; 210/188
(58) Field of Search ................................. 210/646, 645, 210/188, 252; 604/4, 5, 6, 325

(56) References Cited

U.S. PATENT DOCUMENTS

| | | |
|---|---|---|
| 4,293,413 * | 10/1981 | Schnell ................................. 210/188 |
| 4,770,787 | 9/1988 | Heath et al. . |
| 5,041,215 | 8/1991 | Chamberlain, Jr. et al. . |
| 5,520,640 | 5/1996 | Utterberg . |
| 5,650,071 * | 7/1997 | Brugger et al. ....................... 210/646 |
| 5,693,008 * | 12/1997 | Brugger et al. ............................ 604/4 |
| 5,769,815 | 6/1998 | Utterberg . |
| 5,776,338 | 7/1998 | Mari . |
| 5,951,870 * | 9/1999 | Utterberg .............................. 210/645 |

* cited by examiner

Primary Examiner—W. L. Walker
Assistant Examiner—Terry K. Cecil
(74) Attorney, Agent, or Firm—Garrettson Ellis; Seyfarth Shaw

(57) ABSTRACT

A blood processing system (e.g. a dialysis system) having a blood processing unit (e.g. a hemodialyzer) and tubular arterial and venous blood flow sets (10, 14) may be primed by temporarily connecting together the ends of the sets and then passing priming solution in a first flow direction (44) that is retrograde to the normal flow of blood. This causes the priming solution to enter an in-line chamber (64) carried by one of the sets. At the same time, air is removed through a port (62). Preferably, the chamber includes a filter (65). In another step, priming solution is passed through the sets in a second flow direction (42), opposite the first flow direction, while continuing to remove air through the port. Preferably, the solution is passed in the first flow direction by gravity and in the second flow direction with a pump (26a). The solution can also be passed in both directions simultaneously. In another method of the invention, the hemodialyzer (12) is connected to an end of each set after the sets are primed.

18 Claims, 5 Drawing Sheets

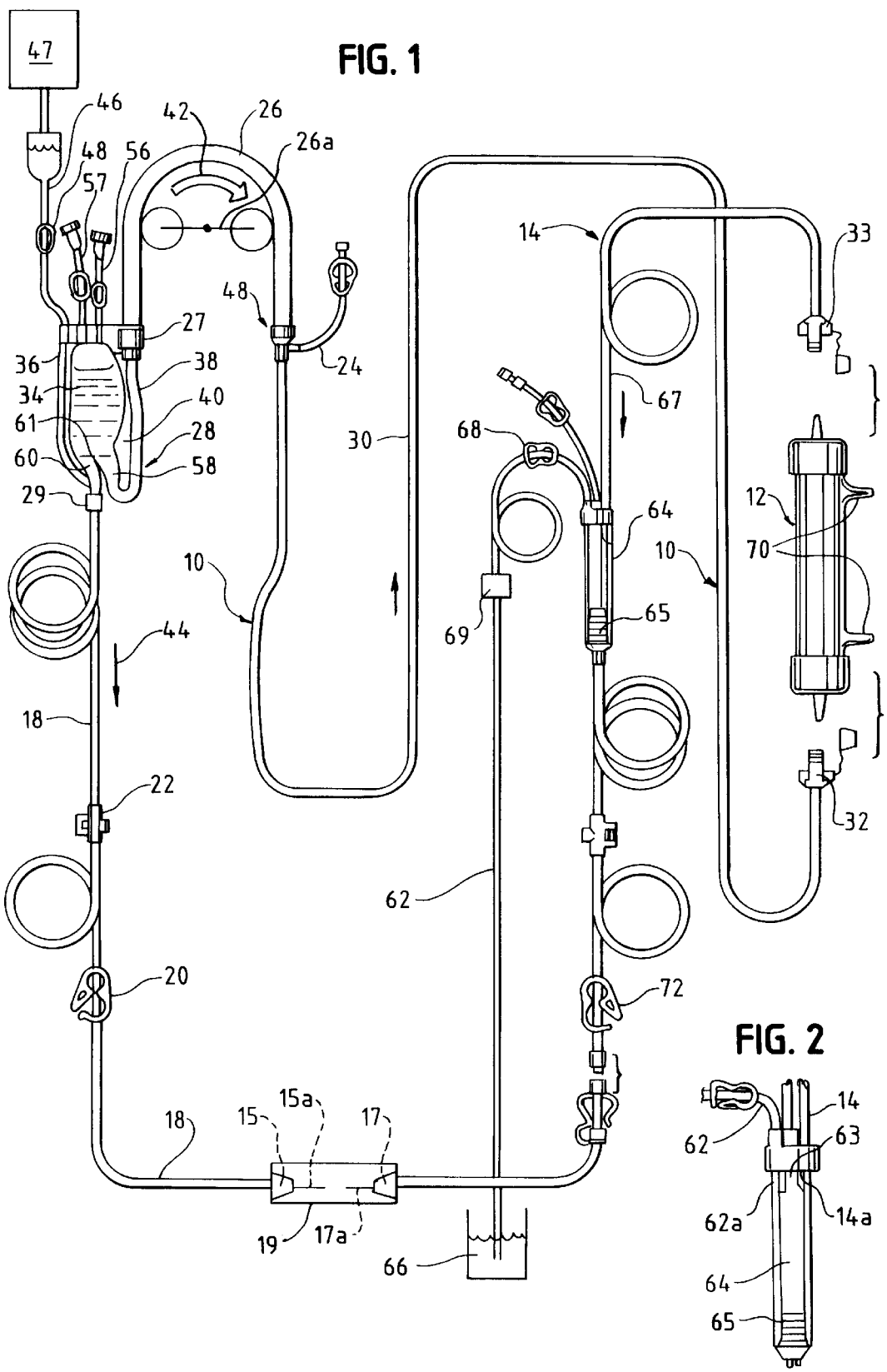

AUTOMATIC PRIMING OF CONNECTED BLOOD SETS

CROSS REFERENCE TO RELATED APPLICATION

This is a division of application Ser. No. 08/954,804, filed Oct. 21, 1997, now U.S. Pat. No. 5,951,870.

BACKGROUND OF THE INVENTION

In hemodialysis and other blood processing treatment, the priming of blood lines leading to a dialyzer from the patient is currently a labor intensive procedure, tying up technicians and nurses from more productive activities.

The blood lines and priming sets are typically provided in "dry" form, while dialyzers are sometimes dry or wet-packed. If reused, dialyzers are wet on each use after the initial use. Wet and dry dialyzers require different priming procedures.

During the priming, the filters, found in chambers of the venous blood sets are difficult to debubble as the sets are primed with saline or other priming solution, because in typical procedures the priming solution comes from above into the venous chamber. Bubbles may remain trapped next to and under the filter of the venous chamber. In current practice, the venous chamber generally has to be turned upside down during part of the priming procedure, to cause the bubbles to pass upwardly through a portion of the venous set and, accordingly, out of the set so that it becomes filled with priming solution in bubble-free manner. During priming, the patient end of the venous set is conventionally placed in an unsterile bucket or drain to catch excess priming or rinse fluid as it drains out of the set. This allows the risk of contamination if the connector at the end of the venous set falls into or otherwise touches the bucket or drain.

At another stage of the conventional priming procedure, the arterial and venous blood lines may be typically connected together via a "recirculation interconnector" for the recirculation stage of the priming procedure. This recirculation "dialyses" out through a connected blood processing unit (dialyzer) contaminants left over from the manufacturing or any reuse process that has preceded the priming.

If the recirculation interconnector is not sterile, another chance for touch contamination of the patient connectors of the respective arterial and venous sets occurs as the respective sets are connected together during the priming procedure by means of such a recirculation interconnector.

This problem is intensified by the fact that the respective connectors of the arterial and venous sets are wet at the time they are conventionally connected with the recirculation interconnector, making contamination by this reconnection a greater likelihood.

In the case of a wet dialyzer (or a re-used dialyzer), the arterial bloodline typically is not connected to the dialyzer until after priming. This prevents air from being introduced into the dialyzer, which might happen in a conventional procedure, but this procedure is less convenient than priming procedures in which both bloodlines are attached to the dialyzer prior to priming.

In conventional priming techniques, the arterial patient connector tube and adjacent tubing may not be adequately rinsed during the priming procedure.

Cobe Laboratories sells the Centry III dialysis machine in which the blood sets may be automatically primed. However, special equipment is required for this automatic priming process. For example, during the process, the blood pump runs backwards for a period of time, thus requiring a blood pump that can pump in either direction. Hence, the Cobe priming process cannot be used with an ordinary dialysis machine to automatically prime arterial and venous sets connected to a dialyzer, if such conventional dialysis equipment has a blood pump that pumps in only one direction. See also Heath et al. U.S. Pat. No. 4,770,787.

Nikkiso Japan has a priming procedure that similarly requires a pump that can be reversed and additionally requires a fluid flow measuring device and timing device to make it automatic.

By this invention, the above problems and inconvenient characteristics can be eliminated or greatly reduced as problems, this being accomplished by a novel method for priming blood sets, which are for use with dialyzers or for use in other blood processing systems.

A partial list of the advantages which can be achieved by this invention is as follows:

1. All flow through prime and blood pathway components of the blood processing system can be connected prior to priming. Particularly, the arterial and venous set patient connectors can be pre-connected in the factory via an interconnector, and sterilized in that form. Thus, the risk of contamination by connector disconnection and later connection to the interconnector is eliminated. Preferably, the interconnector is long enough to receive two fistula needles (or equivalent connectors thereto such as blunt needles or other blood access devices), one extending from each of the patient connectors. Thus, the fistula needles may optionally be in place on the respective sets as received by the user, sterile, and ready for use. Also, the reused system may be reprimed without disconnection of the arterial bloodline from the dialyzer. Also, a dialyzer may be pre-attached to the blood sets, which with pre-attached fistula needles would form a complete extracorporeal circuit.

2. The priming procedure fills the venous chamber and any other filter-carrying chamber of the sets with substantially spontaneous or automatic debubbling, without the need for inverting the chamber or the like.

3. The priming procedure can move from a rinsing mode to a recirculation mode by simply changing the rate of flow of priming solution into the system or the pumping rate through the system.

4. All blood and prime flow pathway segments of the arterial and venous bloodlines are effectively rinsed.

5. No part of the blood pathway comes close to any drain bucket or the like, so that the risk of contamination of the blood pathway from this source is greatly reduced.

6. No special machinery is needed. Particularly, mechanical pumping in two sequential directions through the set is not required.

Thus, a blood processing system is provided in which the priming technique is greatly simplified, with a substantial reduction in both the retention of undesirable air bubbles and in the risk of contamination.

DESCRIPTION OF THE INVENTION

In accordance with this invention, a tubular blood set is provided which comprises a length of blood tubing, having a branch connection with drain tubing that can lead to a fluid drain or receptacle. Typically, this drain tubing is free of permanent physical connection to the drain receptacle, and can be closed off when its use in priming is no longer needed by clamping.

Preferably, this invention relates to a blood processing system which comprises a blood processing unit such as a dialyzer and connected, tubular, arterial and venous sets for blood flow between the unit and the patient. However the blood sets may be primed while connected together without the blood processing unit, and the blood processing unit is then inserted between the sets after priming. Thus priming of the whole system can take place without passing air through a wet, reused dialyzer, thus avoiding trapped bubbles therein.

In its initial configuration for priming, prior to connection with the arteriovenous system of the patient, each of the arterial and venous sets comprises a patient connector at the ends of the sets opposed to set ends that connect (during or after priming) with the blood processing unit. Each of these patient connectors may preferably carry a fistula needle or another access device with the bloodstream of the patient, with the two patient connectors or the access devices being connected by an interconnector, causing them to be in flow relationship which each other. The interconnector may enclose the respective fistula needles or other access devices or said patient connectors. By this, the advantages described above can be achieved.

Further by this invention, a method is provided of priming the above-described blood processing system by the following steps incorporated in a priming process: (1) one passes priming solution in a first direction of flow through at least one of the sets, and preferably portions of both sets including the interconnector, to cause the priming solution to enter an in-line, preferably filter-carrying chamber, carried by the one set, in a flow direction that is retrograde to the normal direction of blood flow through the chamber. One simultaneously removes air or prime from the system through a port that is not a patient connector. (2) In another step, which preferably may be simultaneous with, or alternatively previous or subsequent to the above described step, one passes priming solution in a second, reverse direction of flow to the first direction, preferably through the blood processing unit and connected sets, or the connected sets without the blood processing unit, while continuing to vent air or priming solution from the system through the port.

The priming volume of a tube set and dialyzer is typically 250 cc. or less. Typically, at least 500 ml. of saline is introduced to the set. Thus, about 250 cc. is used in priming, (i.e. only air displacement). The additional 250 cc. of saline is used in overflow rinsing (also called flushing). Thus, priming, or priming and rinsing, of the system is completed.

The second, reverse direction of flow is preferably the normal direction of flow that blood will take through the set during the blood processing procedure, preferably with the aid of a pump rotating in its normal, blood processing direction. Thus, flow may proceed through the set or sets in two directions from the point where the priming solution is introduced, to the air and prime venting port. When the two-direction flow is simultaneous and flow is assisted in the second direction by a pump, priming time can be shortened.

The blood processing unit may be typically be a hemodialyzer, respectively connected at the dialyzer arterial and venous blood ports to the arterial and venous sets, preferably with said dialyzer port positioned below the dialyzer's venous port.

Also, after the air has been removed by priming, it is preferred to connect in the dialyzer if not already connected, and to pass priming solution through the blood processing system and then out of the port, to flush the system. By this procedure, it becomes possible to prime, flush, and "recirculate" all portions of the sets, as well as the blood processing unit (dialyzer) as a second phase of the priming process prior to inserting blood into the system for the processing thereof.

DESCRIPTION OF THE DRAWING

FIG. 1 is a plan view, partially schematic, of a blood processing system of this invention in which the method of this invention may be practiced;

FIG. 2 is an enlarged view of the venous chamber shown in FIG. 1; and

DESCRIPTION OF SPECIFIC EMBODIMENTS

Figure 3:
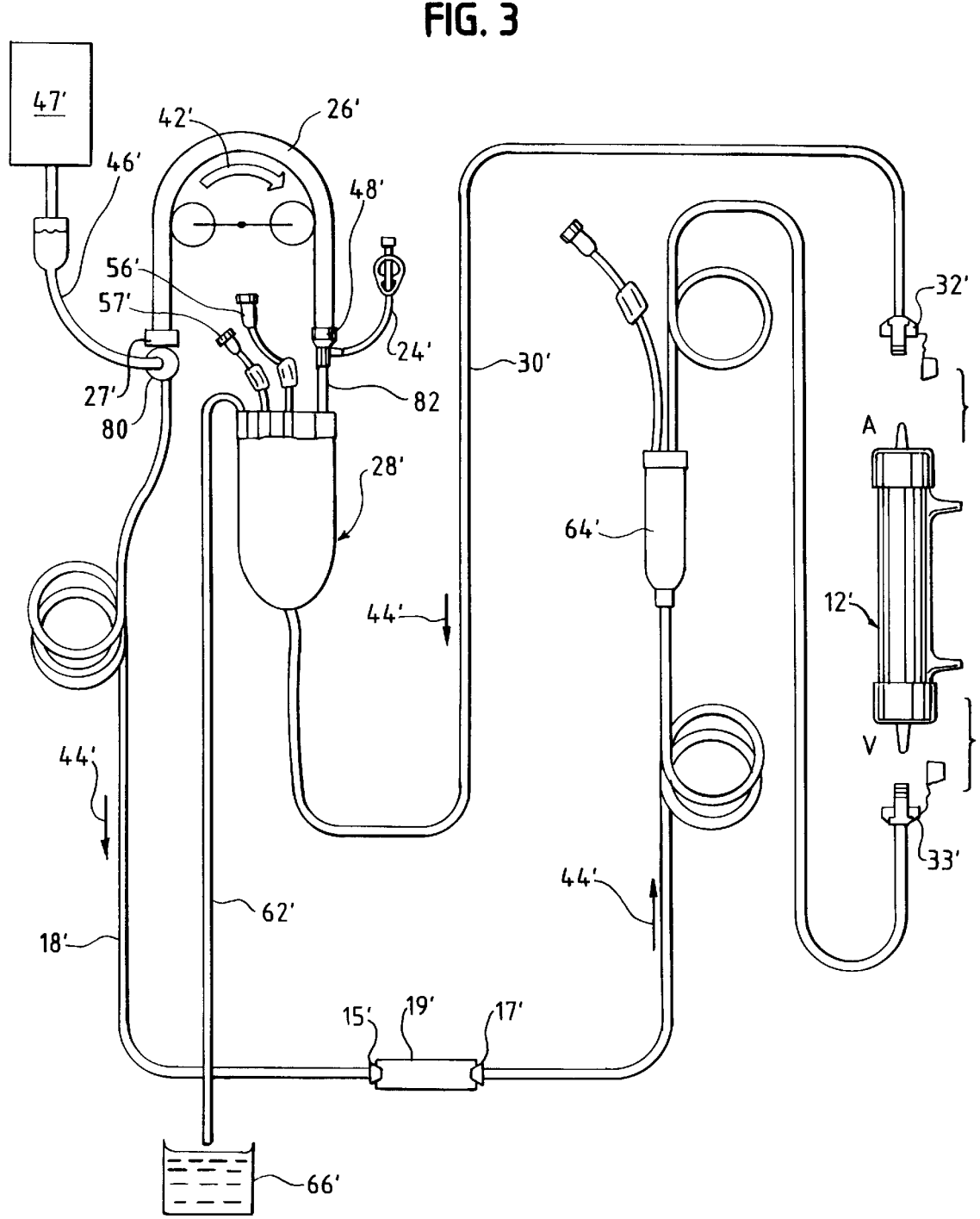
FIGS. 3, 4, 5, and 6 are each plan views, partially schematic, of different embodiments of the blood processing system in which the method of this invention may be practiced.

Referring to FIG. 1, a hemodialysis system is disclosed. The system is similar in some respects to the hemodialysis system disclosed in Utterberg U.S. Pat. No. 5,520,640, except as otherwise indicated herein.

A hemodialysis system is shown comprising an arterial pre-pump set 10 for connection with a conventional hollow fiber dialyzer 12 at one end through connector 32. At the other end of the hemodialyzer 12, a venous set 14 is provided terminating in connector 33. Other, known set-ups may also be used.

Arterial set 10 defines a patient connector 15 which carries a fistula needle 15a, while venous set 14 carries a patient connector 17 which carries a fistula needle 17a. The respective connectors 15, 17, and their carried fistula needles, are temporarily connected together by means of a conventional recirculation interconnector 19, this being preferably accomplished in the factory, with the interior of interconnector 19 and sets 10, 14, being sterile in their form as delivered to the end user.

The set tubing 18 of arterial set 10 extends through an on-off clamp 20, and connects with injection site 22, extending to connect with inlet port 29 of blood chamber 28, a type shown in Utterberg U.S. Pat. No. 5,520,640.

Roller pump segment 26 is shown to be in direct connection with blood outlet port 27 of blood chamber 28, and extends to another pump segment connector 48, and then to tube 30, which extends to connector 32 at dialyzer 12. A heparin line 24 also connects to connector 48. Tubes 56 and 57 also connect to chamber 28. One may connect one of them to a pressure monitor, while the other may be used as an air adjust or medication tube.

Blood chamber 28 may also be a conventional blood chamber of simple, tubular kind, or it may be of a new type such as the type as shown, being made through a blow-molding process of a thermoplastic, so that there may be formed out of a single, plastic, tubular parison the following: reservoir chamber 34 and a pair of attached conduits 36, 38, extending laterally along reservoir chamber 34, being spaced from the chamber by flat-sealed portions 40 of the plastic parison. Conduit 36 connects in branching-relation with blood port 29, and also extends the length of reservoir chamber 34, for connection with I.V. saline access tube 46, which, in turn, communicates with a conventional source of I.V. or priming solution 47. The flow of such solution in the chamber 34 is controlled by pressure clamp 48.

Reservoir chamber 34 can be capable of collapse under a predetermined suction pressure in the manner of prior art blood chambers for the known, desirable purposes, if desired.

Normally, blood is pumped by a roller pump 26a acting on pump tubing 26, flowing from arterial patient connector 15 into reservoir chamber 34. Blood passes through tubing 18 through port 60 into chamber 34, and out of chamber 34 through port 58, which ports are spaced from each other by wall 61. From there, blood flows through pump tubing 26 out of the reservoir chamber, then passing through the remainder of the dialysis set-up, including dialyzer 12 and venous set 14 through dialyzer connector 33, to the venous connector 17, where the blood is returned to the patient.

If desired the dialyzer connectors 32, 33 may be directly connected together during priming without dialyzer 12, using an interconnector like interconnector 19. When air has been removed from sets 10 and 14, dialyzer 12 may be connected in between connectors 32, 33, and the entire system is then flushed with circulating solution as previously described.

In accordance with this invention, the respective components 10, 12, 14, of the blood processing system are connected, and the system is primed by the addition of priming solution from container 47 through line 46 and conduit 36 into chamber 34 by the specific technique described below, particularly when dialyzer 12 is dry. The pump tubing 26 may be installed in a conventional roller pump 26a throughout the treatment.

In one embodiment, roller pump 26a may not initially operate, so that flow cannot take place in the normal, second direction of arrow 42. Thus, initially, flow proceeds downwardly in the first direction 44 as described above through tubing 18 of arterial set 10. As priming solution passes through patient connector 15 and fistula needle 15a, it fills interconnector 19, and continues to flow through venous patient connector 17 and fistula needle 17a. In the meanwhile, air is expelled from the system through drain tube 62, which is connected to the top of venous filter chamber 64 at one end, and may be loosely placed in a receptacle of a dialyzer machine, a bucket, or a drain 66 at its other end, with or without any actual physical connection.

Thus, any contamination that may come to the lower end of drain tube 62 is widely spaced from the blood flow path of the system, and is highly unlikely to climb up drain tube 62, since all flow is out from chamber 64 toward receptacle or drain 66. For example, the lower end of drain tube 62 may be thrown into a sink or a bucket 66.

During this process, all ancillary branching lines may be closed, except typically for the arterial chamber monitor line 56, which may remain open if desired. Clamp 48 may be fully open for maximum flow of priming solution at this point of the process.

Then, when filter chamber 64 has been filled to the desired level by upward flow into it, the roller pump 26a is turned on, pushing the priming solution in the opposite direction 42 toward dialyzer 12 through tube 30. Displaced air continues to flow to venous chamber 64, passing out of drain tube 62.

By this process, all air will be removed from other portions of arterial and venous sets 10, 14, and dialyzer 12. However, referring to FIG. 2, when the air is gone, priming solution will flow into drain tube 62. However, a permanent air bubble 63 can remain in chamber 64 since both tubes 14 and 62 extend into chamber 64 through the top, having respective tube end sections 14a and 62a extending partway down into the chamber so that air-containing area 63 is naturally retained as liquid flows through the chamber via tubes 14, 62.

Alternatively by this invention, priming solution flow may simultaneously move in directions 42 and 44 from inlet area 60, by operating the pump 42 and flowing solution from source 47 into the system at a rate faster than the flow rate of pump 42. Thus, the priming time is shortened.

When venous chamber 64 is filled with liquid, preferably with reverse flow 44 for best bubble removal, and the initial air displacement step of the priming process is completed. Then, the flow rate of the pump 26a is either increased, or the inflow rate of priming solution to chamber 34 from container 47 is decreased, so that the pump flow rate through the system is now greater than the priming solution inflow rate from container 47. This causes flow through tube 18 in direction 44 to cease, with the creation of a second, flushing or rinsing step of circulatory flow through the entire system in direction 42. Residual air continues to be vented by tube 62. This circulatory flow continues throughout the entire rinsing step of the priming process. As added fluid inflow comes from container 47 for such rinsing, fluid is decanted from the system through drain line 62 until about 600 cc. or more of priming solution has been decanted, for good rinsing.

Because of the initial reverse flow into chamber 64, bubbles may have been completely removed from the filter 65 as the solution advances to the filter, without inverting chamber 64 and the tapping techniques that are currently necessary in prior art systems.

Then, the third stage of priming, the recirculation step, may proceed, with the priming solution from source 47 shut off or reduced to a slow drip, and the fluid of the entire system continuing to be pumped in a circulatory flow in direction 42 by means of pump 26a. The flow rate of pump 26a may be increased to a rate of 400–500 ml/min, to dislodge air bubbles from crevices and corners where they may be lodged, facilitated by the upward flow of solution through dialyzer 12. The air bubbles are trapped in the respective chambers 34, 64, and may be removed from there.

Then, when it is desired to displace the priming solution with blood for purposes of dialysis, arterial patient connector 15 with needle 15a can be removed from closure 19, while connector 17 and needle 17a may temporarily remain in the closure 19 to be shielded from contamination. After venipuncture has been made with arterial needle 15a, blood is drawn into the system through tube 18 in direction 42, with the priming solution moving ahead of it. The flow of priming solution from container 47 is typically terminated at this point if not before. The blood passes through arterial set 10 and dialyzer 12, entering into line 67, while clamp 72 may be closed, and the priming solution passes out of drain line 62.

Then, when blood gets to chamber 64, and the air level in chamber 64 is properly adjusted (if needed) clamp 68 of drain tube may be closed and, typically, clamp 68 is not reopened for the duration of the dialysis procedure. The second venipuncture may be made by needle 17a; clamp 72 may be opened; and dialysis proceeds with blood being circulated in direction 42 through the system in conventional manner.

It can be seen that this advantageous priming technique can be used with conventional machinery in which pump 42 pumps in only one direction, and no other special equipment is required. By the use of drain line 64, the sterility of venous connector 17 and needle 17a can be better preserved, since it is placed nowhere near an unsterile bucket or drain during the priming technique, and is shielded prior to use by connector tube 19. Connectors 15, 17 may be inserted into interconnector 19 and sterilized as the set is manufactured, for guaranteed sterility with the respective needles 15a, 17a, attached. This is labor saving, and provides a greater likelihood of sterility for the system.

The drain line 62 may be placed essentially anywhere in the system, although it is desirable to place it at the highest point thereof, as installed in the dialyzer machine, to facilitate the removal of air from the system through drain line 62. Drain line 62 may also carry a one-way valve 69, to assure that there will be no reverse flow of non-sterile fluid through line 62 back into the system.

By this invention, simultaneous priming in directions 42 and 44 can result in a substantial timesaving in the priming process. Then, circulatory flow exclusively in direction 42 can be instituted simply by a reduction in the flow rate of solution from source 47 into the system, or an increase in the circulatory flow rate created by pump 26a, without any necessary disconnections of components of the set, or the like.

The priming technique may be otherwise similar to prior art procedures, if desired. By one such procedure, dialyzer 12 may be flipped so that the arterial connection 32 is on top for dialysis. The dialyzate ports 70 may be connected to dialysis tubing for receiving dialyzate. The flow of the dialyzate is established, and the priming solution within the system of this invention may be circulated at a high pump flow for about 15 minutes, or another time as prescribed by the physician. This is the third stage of priming, discussed above.

A corresponding technique with obvious modifications can be used with a wet dialyzer, while achieving the advantages of this invention. Particularly, set priming can take place without connection to dialyzer 12, as previously described.

By this invention, priming solution flow can approach filter 65 of venous chamber 64 from both directions in the priming procedure described above. The reverse flow priming of the filter 65 substantially eliminates problems of bubbles hanging up in and around the filter, so that there is no need to invert chamber 64 and to take special efforts to remove the bubbles. Also, the risk of contaminating the venous line is effectively eliminated by using drain line 62, which typically connects with the top of venous chamber 64. Likewise, by this invention, the initial, sterile connection during manufacture of the respective arterial and venous patient connectors and fistula needles eliminates a possible source of contamination. Also, the fistula needles 15a, 17a, can be pre-applied if desired for greater simplification of the priming procedure, although they may be applied later by the end user if that is desired. Also, all portions of the arterial patient tube can be well rinsed, contrary to some prior art procedures.

FIG. 3 shows an alternative design of system in which the priming method of this invention can be practiced unless otherwise indicated. Reference numerals of FIG. 3 indicate parts of the system which generally correspond to the numerals of the system of FIG. 1, with the reference numerals of FIG. 3 being delineated by the presence of an apostrophe.

The system of FIG. 3 is similar in structure and function to the system of FIG. 1 except as otherwise indicated herein. Specifically, priming solution from container 47' is fed through line 46' to a connection chamber 80 which also connects with line 18' and connector 27' at the end of pump tubing 26'. Connector 48' at the other end of pump tubing 26' also connects with branch line 24', and a tube segment 82 which enters the top of a bubble trap chamber 28'. Chamber 28' connects with auxiliary lines 56' 57' in the manner of the differently located chamber 28 in FIG. 1, and also connects with tubing 30', which is generally analogous to tubing 30 of the previous embodiment, while accounting for the difference in location in chamber 28'.

Also, this chamber carries at its top drain line 62' which can connect with a drain 66', line 62' and drain 66' being similar in function to the corresponding parts of FIG. 1, but located on the arterial chamber 28' rather than the venous chamber 64 of the previous embodiment. As stated, the remaining components are generally similar to the previous embodiment. The letters "A" and "V" pertaining to dialyzer 12' pertain to the arterial and venous ends thereof, and are reversed from the other embodiments shown.

Arrows 44' pertain to the first direction of priming flow that can take place in the method of this invention, while arrow 42' indicates the second flow direction, which is the normal direction of flow while dialysis is being performed.

It can be seen that drain line 62 is on post pump chamber 28' in terms of normal flow, and thus is under positive pressure. It can also be noted that venous chamber 64' does not have a filter in this instance. Reverse flow in direction 44' can take place to fill dialyzer 12', arterial tubing 30; and chamber 28' until priming solution flows out of drain line 62'. Then, as a second step, the roller pump may be activated to pump priming solution in direction 42' through pump tubing 26' and the remainder of the set in a cyclic pattern, since the patient ends 15', 17' are respectively connected by interconnector 19', for a completion of the process of preparing the system for introduction of blood for hemodialysis.

Figure 4:
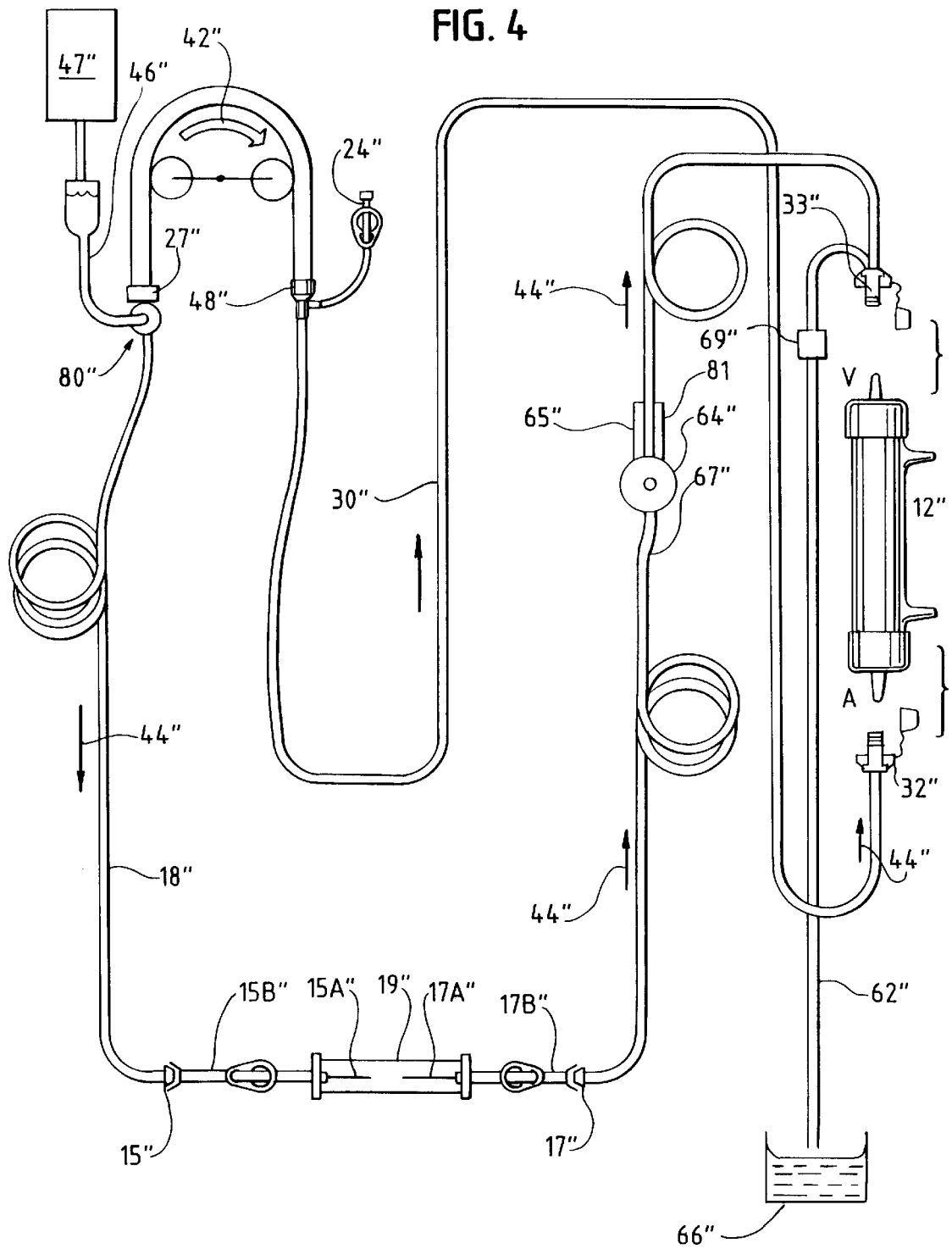

Referring to FIG. 4, another embodiment of the system of this invention is disclosed, in which the reference numerals identify parts that correspond with the parts shown in FIG. 1 having similar reference numerals, but the reference numerals of FIG. 4 are identified with a quotation mark (or double prime).

This system connects prime inlet line 46" to the main circuit between arterial line 18" and pump tubing 42", through pump tubing connector 27" with a simple chamber 80", which typically lacks a planned air space, similar to chamber 80.

In this system, arterial and patient connectors 15", 17" of the respective sets connect to conventional fistula sets 15B" and 17B", which comprise a length of tubing and respective fistula needles 15A" and 17A", which are connected together by a similar, tubular, interconnector 19" as is found in the FIG. 1 embodiment.

Also, chamber 64 of FIG. 1 can be replaced in the venous set of the FIG. 4 embodiment with a chamber 64" that is intended to not contain an air bubble during operation, but is merely used for pressure measurement. An extension of the chamber 64" may contain a filter 65", and the surrounding chamber portion 81 may or may not be sized to receive and trap air bubbles, as may be desired.

In this embodiment, dialyzer connector 33" of the venous set may contain a branch line which comprises drain line 62", similar in function to drain lines 62 and 62' of the previous embodiments but at a different location.

Thus, when prime solution from container 47" is moving in the first direction 44", which is retrograde to the normal direction of flow, priming solution approaches filter 65" from the bottom to immerse it with prime with few or no residual bubbles trapped by the filter. This can be accomplished without the conventional need of inverting the filter and tapping.

It can be seen that the arterial and venous ends of dialyzer 12" are the same as the ends of dialyzer 12 in FIG. 1.

The dialysis system of FIG. 4 may be primed and prepared for hemodialysis in accordance with the previous description.

Figure 5:
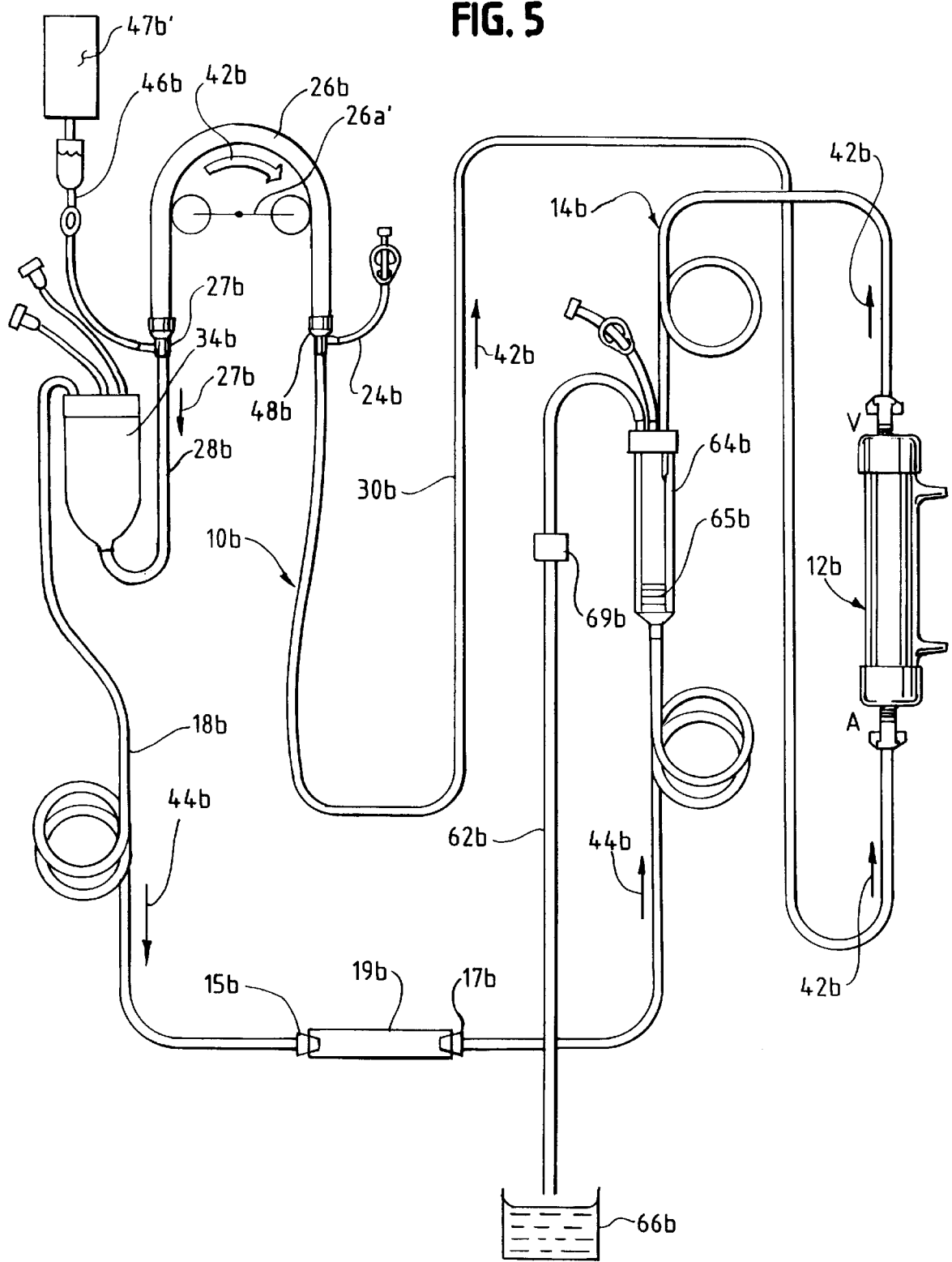

Referring to FIG. 5 another dialysis system is shown, which is similar in structure and function to the previous embodiments except as otherwise indicated herein. The reference numerals identify parts that correspond to the previous parts of FIG. 1, except that the corresponding reference numerals of FIG. 5 are identified with the suffix b.

In FIG. 5, chamber 34b is a conventional chamber having a bottom exit which connects with separate tubing 28b which, in turn, leads through pump tubing connector 27b to the pump tubing 26b. The first flow direction 44b is shown by various arrows, in which priming solution passes from source 47b, but in this case to a branch connection which is part of pump connector 27b. From there, in the first flow direction 44b of priming, prime enters chamber 34b from the bottom and thence via arterial line 18b through connectors 15b, 17b to the venous set and chamber 64b which carries filter 65b in a manner similar to the embodiment of FIG. 1.

Simultaneously or sequentially, pump 42b can pump prime in the second direction 42b for expedited priming as previously discussed. If the two directions of flow 42b, 44b are simultaneous, this can be controlled by providing a greater inflow rate to the system through connector 27b than the pumped flow rate through pump tubing 26b, for simultaneous flow in directions 42b, 44b, as shown. Thus, filter 65b can be immersed in prime from the bottom up, which facilitates the removal of bubbles from the filter area. Drain line 62b is provided in the position similar to that of FIG. 1 for the purposes previously described.

Figure 6:
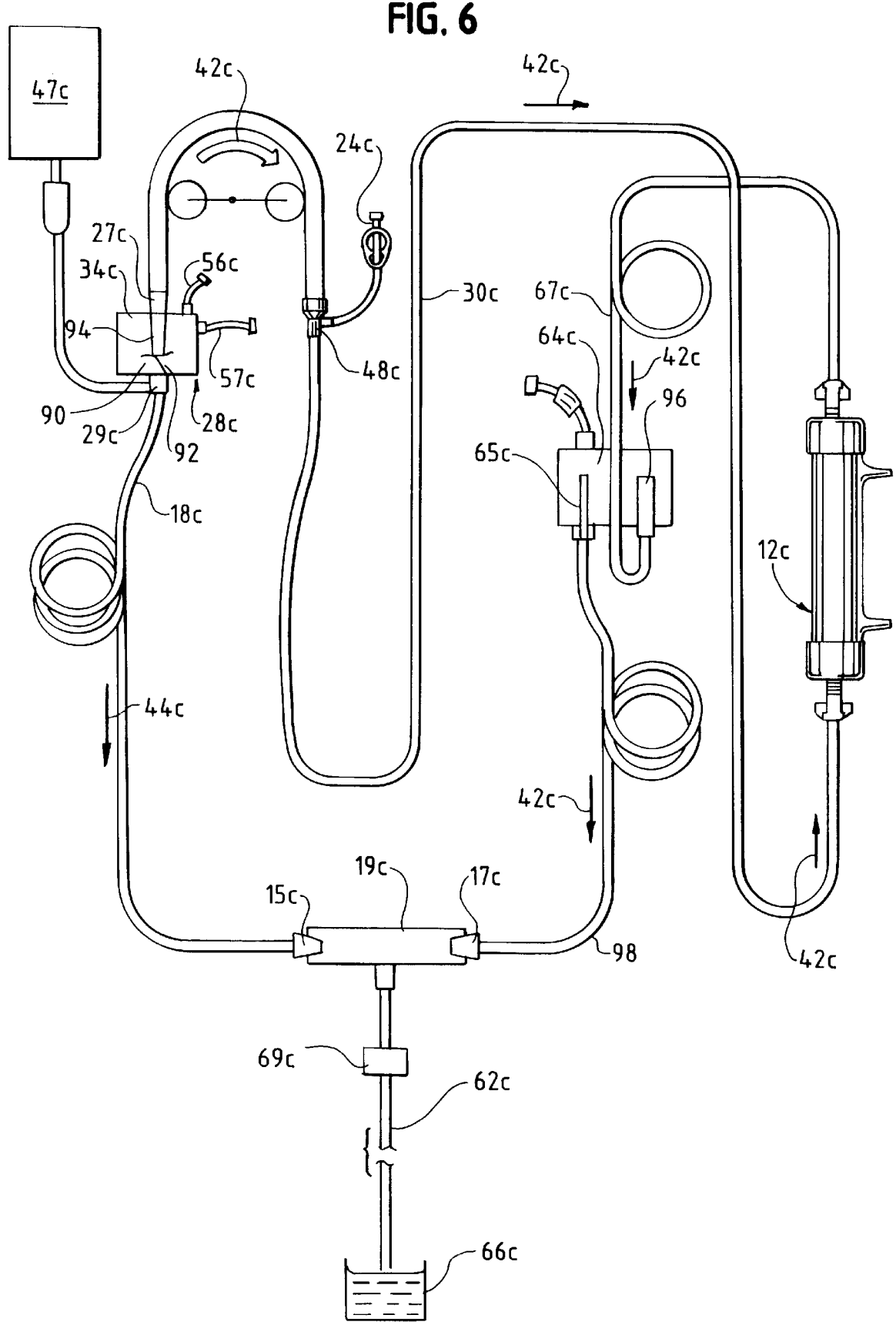

Referring to FIG. 6, another dialysis system is shown, being similar in structure and function to that of FIG. 1 except as otherwise indicated. The parts indicated by reference numerals of FIG. 6 are similar to the parts indicated by the corresponding numerals of FIG. 1, with the reference numerals of FIG. 6 being identified by the suffix "c"

As one significant difference of the system of FIG. 6, drain line 62c is connected between the ends 15c, 17c of the respective arterial and venous sets, being in branching connection with tubular inner connector 19c. Drain line 62c performs a similar function to the corresponding and previous drain lines 62 despite being at a different location in the system. Also, bubble collection chambers 28c and 64c are similar in their purpose to the respective bubble collection chambers 34, 64 of FIG. 1. However, bubble collection chambers 34c, 64c are each wider than they are tall, to provide a substantially horizontal flow of fluid through the chambers, which better allows the rising of bubbles to the top of the respective chambers as more particularly described in Utterberg patent application Ser. No. 08/775,806, filed Nov. 26, 1996 and entitled Wide Bubble Traps.

Arterial line 18c and connector 29c connect with bottom area 90 of the interior of chamber 34c, which is separated by a partition from area 92 of the chamber. Thus, flow into chamber from line 18c in direction 42c must flow horizontally to the left of the chamber interior 34c, and then swirl around before it comes to area 92 after substantial horizontal flow. At area 92, it is drawn into tubular portion 94 and from there into pump tubing 42c.

With respect to chamber 64c, fluid inflow from venous line 67c enters the bottom of chamber through closed end tube 96, which directs fluid flow horizontally to the right in chamber 64c in generally horizontal flow away from filter 65c, which connects with outlet line 98 that communicates with venous patient connector 17c. Thus, in both chambers 34c, 64c, a substantially horizontal fluid flow is provided, which facilitates the rising of bubbles to the top of the respective chambers.

As before, inlet flow of priming solution can travel simultaneously (or sequentially) in two different directions 42c, 44c for priming and subsequent preparation of the set for blood dialysis, as previously described.

The above has been offered for illustrative purposes only, and is not intended to limit the scope of the invention of this application, which is as defined in the claims below.

That which is claimed:

1. The method of priming a blood processing system comprising connected tubular arterial and venous blood flow sets, for connection between a blood processing unit and a patient, which method comprises:

passing priming solution into and through said connected sets in a first flow direction that is reverse to the normal direction of blood flow through said sets, while removing air from said sets through a port communicating with the sets; and passing priming solution in a second, reverse direction of flow to said first direction through said sets while continuing to remove air from the sets through said port, said method including the characteristic of pumping said solution with a flow pump through said system in only the reverse flow direction, and not in the first direction, during the entire priming process, said sets being temporarily connected together at least one of respective ends thereof throughout the entire priming process.

2. The method of claim 1 in which said blood processing unit is a hemodialyzer.

3. The method of claim 1, which further comprises passing priming solution through said blood processing system and then out of said port to flush said system.

4. The method of claim 1 which comprises simultaneously passing priming solution in said first and second directions in different parts of said sets.

5. The method of claim 4 comprising the step of passing said solution in the second direction using said flow pump, and passing said solution in said first direction using gravity.

6. The method of claim 5 in which, thereafter, flow in the first direction is terminated but is continued in the second direction in a complete circuit through said blood processing system by adjustment of flow rates of at least one of the flow pump and the inflow rate of priming solution.

7. The method of claim 1 comprising the step of passing said solution in the second direction using a flow pump, and passing said solution in said first direction using gravity.

8. The method of claim 1 in which said blood processing unit defines an arterial (blood inlet) connection with said arterial set at a bottom portion of said unit.

9. The method of claim 1 in which said blood processing unit is connected to each of said arterial and venous blood flow sets during said priming.

10. The method of claim 1 in which said arterial and venous blood flow sets are connected with each other without an intervening blood processing unit during said priming, and said blood processing unit is thereafter inserted between the arterial and venous blood flow sets.

11. The method of claim 10 which comprises the step of passing said solution in the second direction using a flow pump, and passing said solution in said first direction using gravity, and, thereafter, terminating flow in the first direction while continuing flow in the second direction in a complete circuit through said joined arterial and venous flow sets by adjustment of the flow rates of at least one of the flow pump and the inflow rate of priming solution.

12. The method of priming a blood processing system comprising connected tubular arterial and venous sets for subsequent connection and blood flow after said priming with a blood processing unit, said sets, and a patient, which method comprises the following steps:

a. passing priming solution into said system in a first direction of flow through portions of both said arterial and venous sets which are temporarily connected together at respective ends thereof, to cause said priming solution to enter an in-line chamber carried by one of said sets, said first flow direction being retrograde to the normal direction of blood flow through said chamber, while removing air from said sets through a port positioned in flow connection with said sets;

b. passing priming solution in a second, reverse direction of flow to said first direction through different portions of said system while continuing to remove air from the system through said port; and c. connecting ends of said arterial and venous sets with said blood processing unit.

13. The method of claim 12 which further comprises passing priming solution into and through said blood processing system and then out of said port to rinse said system.

14. The method of claim 13, which comprises simultaneously passing said priming solution in different parts of said system in the first and second directions of flow.

15. The method of claim 14 comprising the step of passing said solution in the second direction using a flow pump, and passing said solution in said first direction using gravity.

16. The method of claim 15 in which, thereafter, flow in the first direction is terminated but is continued in the second direction by adjustment of flow rates of at least one of the flow pump and the inflow rate of priming solution to said system.

17. The method of claim 12 in which said chamber carries a filter.

18. The method of claim 12 in which said port is positioned between the ends of one of said sets.

* * * * *